United States Patent [19]

Chikazawa et al.

[11] Patent Number: 4,550,076
[45] Date of Patent: Oct. 29, 1985

[54] RAPID ASSAYING METHOD FOR GUANASE

[75] Inventors: Nobumoto Chikazawa, Nara; Toshiharu Muraoka, Nagaokakyo; Setsuro Fujii, Toyonaka, all of Japan

[73] Assignee: Maruho Co., Ltd., Osaka, Japan

[21] Appl. No.: 424,182

[22] Filed: Sep. 27, 1982

[30] Foreign Application Priority Data

Sep. 25, 1981 [JP] Japan ................. 56-152807

[51] Int. Cl.$^4$ .................. C12Q 1/34; C12Q 1/26; C12Q 1/28
[52] U.S. Cl. ...................... 435/18; 435/25; 435/27; 435/28
[58] Field of Search ............ 435/4, 18, 25, 26, 27, 435/28

[56] References Cited

PUBLICATIONS

Slowiaczek et al., Anal. Biochem., 125: 6–12, (1982).
Kato et al., Chemical Abstracts, 92: 159394c, p. 204, (1980).
Sugiura et al., Chemical Abstracts, 94: 169969z, p. 288, (1981).
Ando et al., Chemical Abstracts, 98: 156866w, p. 183, (1983).
van Bennekom et al., J. Clin. Chem. Clin. Biochem., 16: 245–248, (1978).
Roush et al., Arch. Biochem., vol. 29, pp. 124–129, (1950).
Hue et al., Clin. Chem., vol. 11, pp. 708–715, (1965).
Kalcker, J. Biol. Chem., vol. 167, pp. 429–459.

Primary Examiner—Esther M. Kepplinger
Attorney, Agent, or Firm—Armstrong, Nikaido, Marmelstein & Kubovcik

[57] ABSTRACT

The guanase activity in body fluids such as blood serum can be rapidly and accurately assayed by (I) decomposing guanine with the guanase in the specimen to xanthine and ammonia at pH 7–9, preferably at pH 8, (II) decomposing the xanthine formed by former step I with xanthine oxidase to uric acid and hydrogen peroxide, (III) reacting the reactant solution of the former step II with 3-methyl-2-benzothiazolinonehydrazone, an aniline derivative such as N,N-di-lower-alkylaniline and peroxidase, and finally measuring the optical absorption of the reactant solution of the step III at 570–600 nm. The all steps can be completed within 15 minutes. Therefore, this assay is adoptable for automatic assay of guanase on usual clinically available automatic analyzers.

6 Claims, 5 Drawing Figures

RAPID ASSAYING METHOD FOR GUANASE

FIELD OF THE INVENTION

This invention relates to a rapid assaying method for guanase in the body fluid.

BACKGROUND OF THE INVENTION

Guanase is an important enzyme which catalyzes the conversion of guanine to xanthine in the nucleotide metabolism of living bodies. As shown by the following formulae, in the higher animals, the xanthine formed by this enzyme is oxidized to uric acid, but in the lower animals, said uric acid is further decomposed to allantoin and thereafter exhausted as urine.

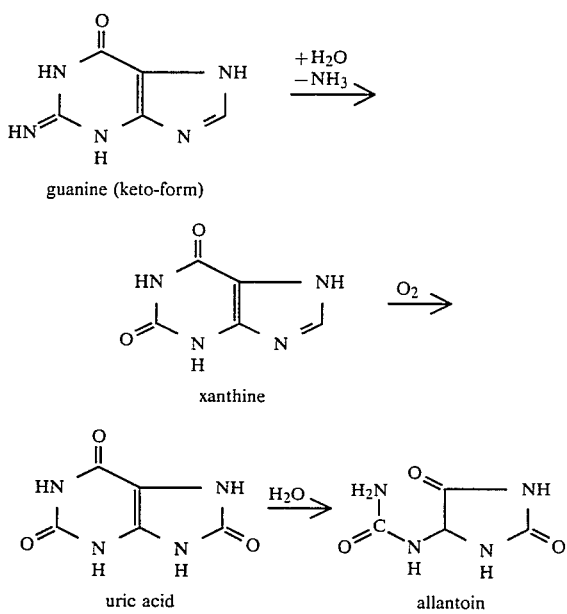

As the progress of the diagnostic medicine continues, the pathological inspection of the body fluids such as serium has now become important. Thus, in the diagnosis of liver diseases, there are several inspections for estimating the activity of enzymes, such as transaminase (COT,GPT), alkaliphosphatase and gamma-glutamyl-transpeptidase (gamma-GTP) which have been broadly carried out. Among these tests, transaminase and alkaliphosphatase seem not to be good parameters for the liver diseases since they are broadly distributed in the body tissues other than the liver. On the other side, the latter gamma-GTP is valuable for diagnosis of the liver diseases since it is known to be peculiar for the liver diseases (Szasz, G., Rosenthal, P. and Fritzsche, W.; Dt. Med. Wschr., 94, pp. 1911-1917(1969)). Although this gamma-GTP has become an important parameter for the diagnosis of chronic hepatitis, cirrhosis and obstructive jaundice since it keenly reflects to biliary injuries, it is almost inactive to an acute hepatitis. (The titer of this enzyme is almost unchanged by the latter disease.) (Fujisawa, K.; Gan TO Kagakuryoho (Cancer and Chemotherapy) 5, suppl. II, 373–379(1978)). Thus, the assay of this enzyme is not available for the diagnosis of acute hepatitis.

Contrary to the former, it has been known that the titer of guanase is particularly raisen in case of the acute viral hepatitis but is almost not unchanged in case of/-chronic hepatitis and cirrhosis (Whitehouse, J. L., Knights, E. M., Santoz, C. L. and Hue, A. C.,: Clin, Chem., 10, p.632(1964); Bel, A., et al.: Presse. Med., 78, pp. 495–499(1970)). Therefore, the assay of the titer of this enzyme is available for the diagnosis of acute viral hepatitis as a reliable tool.

Moreover, the hepatitis followed by blood transfusion which has become a serious social problem is almost caused by non-A and non-B viruses. However, any effective screening method for the protection of these kinds of hepatitis has not been discovered. Recently, it however has become clear that such hepatitis can considerably prevented, if only the blood for transfusion can be preliminarily screened as to the titer of guanase. Thus, the assay of guanase is also useful for preventive medicine.

In turn, according to the increase in the diagnostic value of this enzyme, there are increasing needs for automatic assay of it. However, because of lower titer of this enzyme in normal human blood serum and considerable long time needed for assay, there has heretofore not been existing any appropriate automatic means for assaying this enzyme. Namely, in the present clinical measurement, highly automated analysers are positively introduced. According to such analyser, various kinds of assays are paralelly carried out so as to complete whole assays within 10–15 minutes per each sample. Thus, it is practically impossible to prolong the assaying time only for guanase. Alternatively, even if such prolongation is possible, practice of such alteration makes the introduction of expensive automatic analyser meaningless. In this connection, the assay of guanase has not become common for routine clinical assay.

The object of the present invention is to surprisingly shorten the necessary time for assaying guanase without lowering accuracy by improving known methods used heretofore for assaying this enzyme and to make it possible to introduce said method to an automatic analyzer.

In turn, known representative assaying methods for guanase are enumerated as follows:

(1)
Roush-Norris Method (Roush, A. and Norris, E. R.; Arch. Biochem, 29, pp.124–129(1950)): This method is based on the difference in the optical absorption between guanine and xanthine. The decreasing rate of guanine is assayed.

Hue-Free Method (Hue, A. C. and Free, A. H.; Clin. Chem. 11. pp.708–715(1965)) is an improvement of above-mentioned method, wherein the measurement is carried out in a borate buffer in order to remove the influence of xanthine oxydase in the sample. (Absorption strength (Molar absorption coefficient) ($\epsilon$)=$0.535 \times 10^4$.)

(2)
Kalcker method (Kalcker, H. M.; J.Biol. Chem., 167, pp. 429–444, 445–459): In this method, xanthine produced from guanine is furthermore oxidized to uric acid by milk xanthine oxidase. The amount of the uric acid formed is measured by the change of the absorption at 290 nm. $\epsilon = 1.23 \times 10^4$ (3)
Ammonia-assay method
(i) Ellis-Goldberg Method (Ellis, Graham and Goldberg, David M.; Biochem. Med., 6, pp. 380–391(1972)): In this method, the amount of ammonia by-produced when xanthine is formed from guanine is estimated. The assay of ammonia is carried out by reacting alpha-ketoglutaric acid and NADH (reduced type of nicotinic acid amide adeninedinucleotide) with producing ammonia under the exsistence of glutamate dehydrogenase and estimating the amount of NADH consumed. $\epsilon = 0.622 \times 10^4$ (ii) Ito et al. Method (Susumu Ito, Masahiro Kagawa, Tutomu Kanbara and Takeshi Murakami; Rinshobyori (Clinical Pathology); 23, pp.733–736(1975)): In this method, the amount of the ammonia formed is assayed by utilizing indophenol reaction. $\epsilon = 1.96 \times 10^4$ (4) Hydrogen peroxide-assay Method In this method, the amount of the hydrogen peroxide by-produced by the practice of above Kalcker method is measured.

(i) Fritz et al. Method (Fritz, Heintz, Reckel, Sylvia and Kalden, Joachim R.; Enzyme, 24 pp.247–254 (1979)): In this method, the hydrogen peroxide is subjected to the action of catalase under the presence of ethanol to form acetaldehyde, which is then reacted with NAD (Oxidized type of nicotinic acid amide adeninedinucleotide) and acetaldehyde dehydrogenase to form NADH. The change in the amount of the NADH is determined for the assay. $\epsilon = 0.624 \times 10^4$ (ii) Sugiura et al. Method (Kenji Kato, Tetsuo Adachi, Yoshimasa Ito, Kazuyuki Hirano and Mamoru Sugiura; Lecture Abstract of Sympodium for Analitical Chemistry of Ingredients in the Living Bodies, Japan Pharmaceutical Society Press, pp. 41–44 (1979)): In this method, hydrogen peroxide is reacted with 3-methyl-2-benzothiazolinonehydazone (MBTH), dimethylaniline (DMA) and peroxidase to form an indamine pigment which is then assayed according to a colorimetry. $\epsilon = 3.37 \times 10^4$ (5) Radioisotope Method (Van Bennekom, C. A., Van Laarhoven, J. P., De Bruyn, C. H. M. M. and Oei, T. L.; J. Clin. Biochem., 16, pp.245–248(1978)):

This method uses a labeled guanine with $^{14}C$ and xanthine formed is separated by an electrophoresis, and then the radioactivity of the latter is measured by a scintilation counter. This method has high accuracy but it also requires special equipment and expertise since it uses dangerous $^{14}C$. Therefore, this is hardly available for common clinical test. As hereinbefore described there are many methods for the estimation of guanase activity, however, normally the guanase activity in human blood serum is usually 1-2 IU/1 (1 IU corresponds to the activity of decomposing 1 $\mu$mol of substrate per minute at 37° C.) so that the value should be over $2 \times 10^4$ in order to complete the reaction within 15 minutes. Among all methods mentioned, only Sugiura method of (4)(ii), above is satisfactory to this condition. However, this method has a essential defect that it can not exclude the effect of catalase in serum and therefore it can not reflect on true titer of guanase. Namely, since sodium azide added as the catalase inhibitor does not completely inhibit the catalase activity, if hydrogen peroxide is co-existed with catalase during reaction time, the data will naturally become incorrect. Moreover, the guanase reaction, wherein the substrate is decomposed, is carried out at pH 6.2 in order to stabilize hydrogen peroxide.

The optimal pH of guanase however is approximately at pH 8.0 so that the enzyme exerts about 60% activity as compared with that of the optimal one. This fact causes the prolongation in the reaction time.

SUMMARY OF THE INVENTION

We have earnestly directed to the solution of these problems and made endevour for establishing new assay of guanase applicable for automatic assay. As the results of continuous investigations, we have now succeeded in creating a novel assay by which the guanase can be assayed within 15 minutes with high accuracy and high stability of the reagents. The present invention essentially includes the following three steps:

(I) Guanase reaction step (xanthin-formation step): In this step, the sample solution is added into a buffer solution of substrate (guanine) (pH 7–9) followed during incubation for 10–30 minutes by which the substrate is decomposed to xanthine and ammonia by the action of the guanase in the sample.

(II) Hydrogen peroxide-formation step: In this step, a buffer solution of xanthine oxidase (pH 7–9) is added to the reaction solution of (I) and the xanthine formed by the foregoing step (I) is decomposed to uric acid and hydrogen peroxide.

(III) Coloring reaction step: To the reaction solution of (II), there are simultaneously added MBTH, an aniline derivative and peroxidase so as to form an indamine dye. The foregoing steps can be illustrated by the following scheme:

The first (I) step

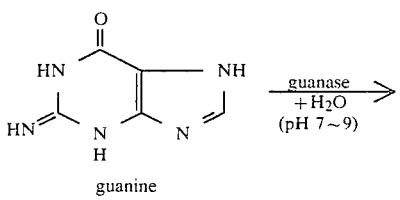

guanine

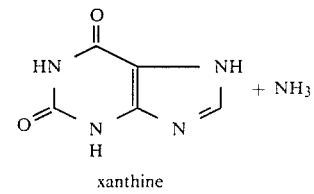

xanthine

The second (II) step

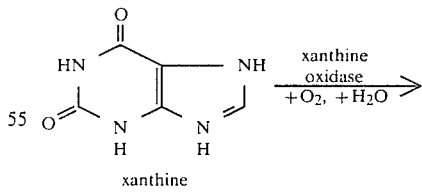

xanthine

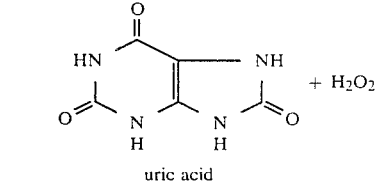

uric acid

The third (III) step

-continued

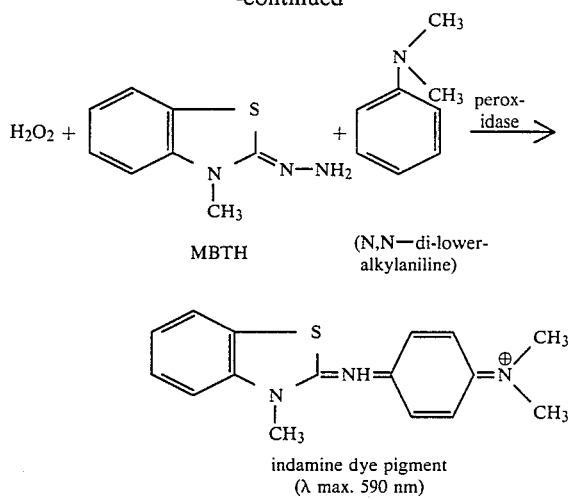

MBTH (N,N—di-lower-alkylaniline)

indamine dye pigment
(λ max. 590 nm)

Among the above three steps, the most important is that A; the steps consist of the three procedures that is, the guanase reaction of (I), the hydrogen peroxide-formation reaction of (II), and the coloring reaction of (III) and B: the guanase reaction of the step (I) is carried out at pH 7-9, preferably a pH 8 near side.

In the Sugiura method afore-mentioned, this guanase reaction is simultaneously carried out with the next hydrogen peroxide-formation reaction, so that the reaction should be done at pH 6.2 apart from the optimal pH of the guanase. In this connection, the reaction of them takes long time and moreover the reaction is influenced by catalase whereby the result becomes incorrect. On the other hand, in the present invention, the reaction is divided into I and II, whereby the step I can be carried out at about pH which is optimal for the guanase. Therefore, the reaction of this invention may be carried out within 15 minutes which is the threshold time for automation.

DETAILED EXPLANATION OF THE DRAWINGS

DETAILED EXPLANATION OF THE INVENTION

Figure 1:
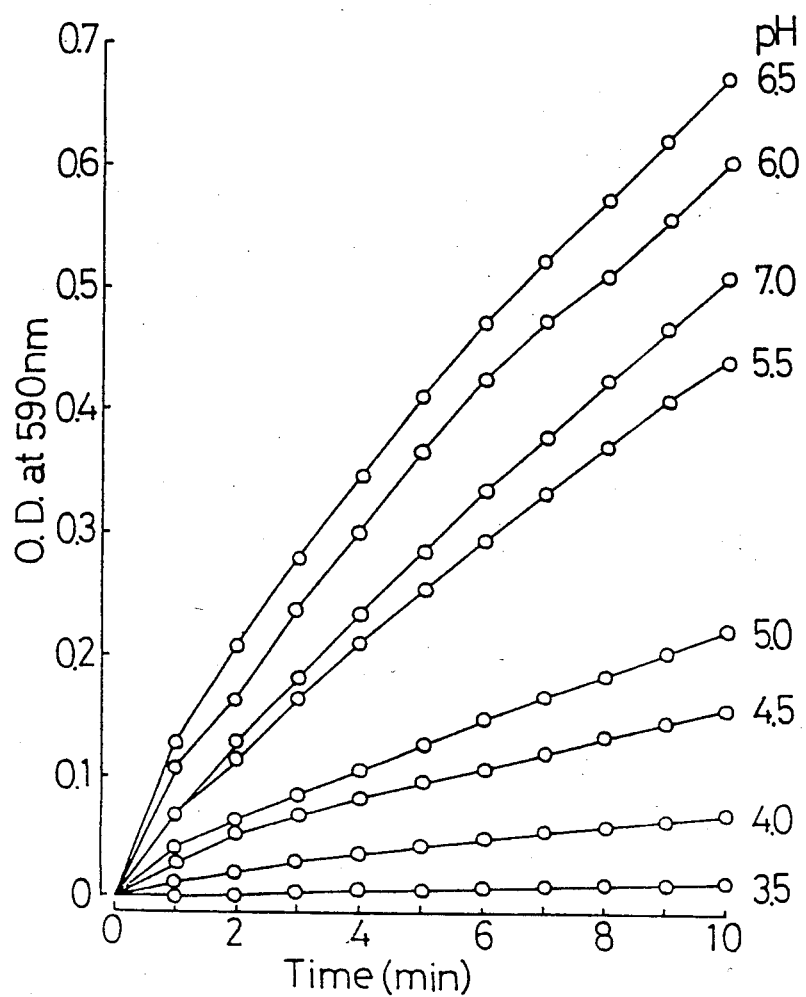
FIG. 1 is a graph showing the relationship between the stability of the chromogenic solution and pH in the present invention.

Other than previously explained, other conditions necessitated for mounting the present assay on clinical routine test are to stabilize the chromogenic solution and to make the calibration line linear. That is, the xanthine oxidase derived from milk used in the step II does not directly form hydrogen peroxide different from common oxidase and it intermediately forms the super oxide radical ($O_2^-$) which changes spontaneously to hydrogen peroxide. Therefore, in the course of this change, if an electron receptor is existing, it will give the electron to such receptor (that is, a reduction is caused.) In this connection, if both the systems of hydrogen peroxide-formation and coloring reactions are joinly present (in other word, if the hydrogen peroxide-formation reaction and the coloring reaction are simultaneously carried out), the dye once formed will be discolored and therefore the calibration line will be curved. However, if the step II and III are divided in order to prevent such defect, then another fear that true guanase activity might not be estimated by the action of catalase or the like in serum will be arosen.

We however have found, as the result of further investigation, that the above paradox can be solved by adding a catalase inhibitor to the reaction solution of the substrate and further shortening the time for hydrogen peroxide-formation reaction. Accordingly, in the present invention, it is necessary condition that the hydrogen peroxide reaction of the step II is carried out in the presence of a catalase inhibitor and as rapid as possible.

The present assay of the invention can be usually conducted by utilizing an automatic analyzer. Now, there are several kinds of automatic clinical analysers commercially available. Thee analysers are wholely equipped with an intermittently rotating endless chain or disk on which many test tubes are being mounted with an equal interval, a stational measuring station, and/or CRT display, etc. The samples (blood specimen) are equally poured into respective tubes, incubated for a destined time and then assayed by the measuring station. The data thus obtained is then printed out through a transaction means and/or displayed on a Braun tube of the CRT display. On the other hand, the test tubes which have been assayed over are then washed dried and further receive new samples for the succeeding assay. In the present analysers, the equipment are designed to assay a sample parallelly on items such as alkaliphosphatase, glutamic acid-oxaloacetic acid transaminase, glutamic acid-piruvic acid transaminase, leucine aminopeptidase, triglycerides, glucose etc. (within 15-30 minutes from the set of the samples to the completion of the assay). Therefore, as hereinbefore described, it is impossible to extend the assaying time for specific item(s). Thus, catalogues of such analysers are used to neglect the assay of guanase. According to the present invention, the assay of the guanase however has become possible. Therefore, to assay the guanase activity by an automatica analyser is included in the important object of the invention. The fundamental object of the present invention is to shorten the time required for the assay of guanase and further to accurate the result of this assay, and such effect can naturally attained even by manual operation. Therefore, the use of the automatic analyser per se is not the essential element of the present invention.

In the step I (the xanthin-formation stage or guanine reaction step), an alkali solution to which the substrate (guanine) and a catalase inhibitor (for example, sodium azide) are solved, is joined with McIlvain buffer solution (sodium secondary phosphate-citric acid) immediately before the use to prepare the substrate buffer solution. The pH of this buffer solution is selected within a range of pH 7-9, preferably pH 8 near aside which is optimal pH for guanase. As an inhibitor, such compounds as will reversely combine with the Fe-porphyrin activity center of catalase such as cyano compounds, fluoro compounds etc. are also examined, however, in the present invention, an azide compounds such as sodium azide is preferred in consideration of the influence to the guanase.

In the hydrogen peroxide-formation reaction of the second step II, xanthine oxidase suspended in ammonium sulfate solution and buffer solution used in the former step I are blended and added to the reaction solution of the step I, and allowed to stand for a short time (for example, one minute). The catalase inhibitor may be added during this step.

In the step III, McIlvain buffer (pH 3.0) containing MBTH and an aniline derivative, is mixed with peroxidase at the use and the mixture is added into the reactant solution of the step II. The reaction will be completed within one minute. As the aniline derivative usable, N,N-di-loweralkyl aniline, such as N,N-dimethylaniline, N-N-diethylaniline, N,N-di-n-propylaniline etc. is preferred.

Experiment 1

0.1 ml of McIlavain buffer solution (in which the pH is serially changed at pH 0.5 interval), 0.3 ml of 150 mM diethylaniline (DEA), 0.15 ml of 5 mM MBTH, 0.3 ml of 8 m U xanthine oxidase, 0.3 ml of 15 U peroxidase and 0.4 ml of distilled water were admixed and warmed at 37° C. To this mixture, 50 $\mu$l of human serum were added and the optical absorption of this mixture was traced with an interval of one minute. The result is shown by FIG. 1 attached. As shown by the figure, the optical absorption increases as the rise of the pH of the chromogenic solution and the increase of times elapsed. The increase in absorption is remarkable at over pH 4.0. Therefore, the pH of the chromogenic solution is preferablly lowered less then 3.5.

Experiment 2

(The state of coloring when hydrogen peroxide-formation reaction and coloring reaction were carried out simultaneously)

Figure 2:
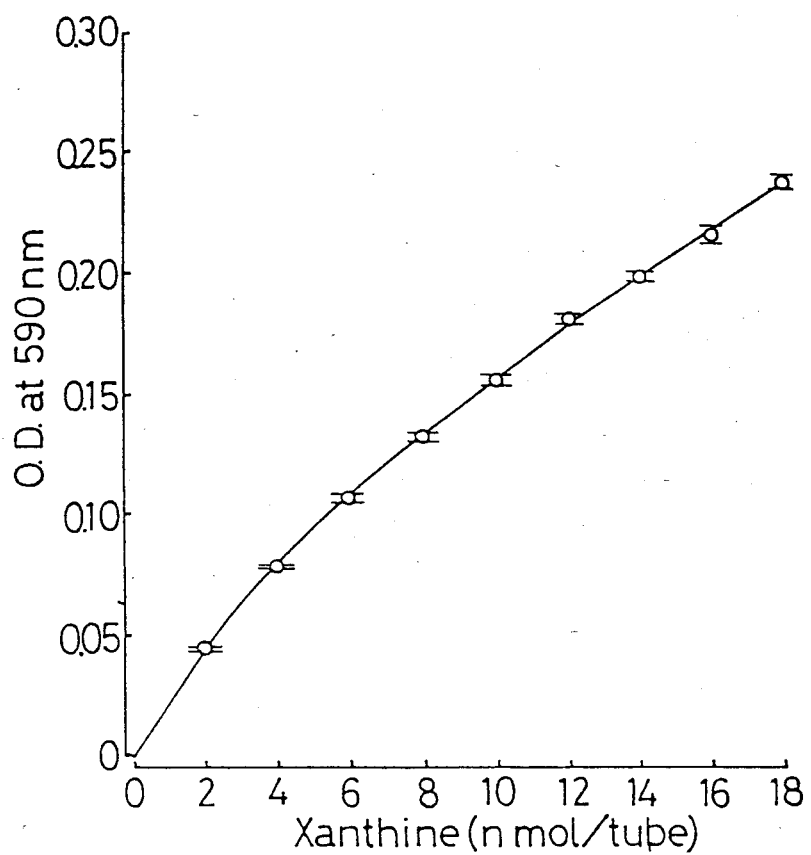
FIG. 2 is a graph showing the relationship between the concentration of xanthine and the producing color when the hydrogen peroxide-formation reaction and the coloring reaction are simultaneously carried out.

To 50 $\mu$l of human serum, there was added 0.45 ml of 0.3 mM guanine buffer solution (pH 8.0) and incubated for 15 minutes at 37° C. To this reaction mixture, a buffer solution (pH 4.0) containing 0.5 mM of MBTH and 30 mM of DEA and 0.2 U of xanthine oxidase (X.O) and 5 U of peroxidase (POX) were added and then incubated for 5 minutes at 37° C. followed by the measurement of the coloring by the absorption at 590 nm. The result is shown by FIG. 2. The short lines holding the upper and lower sides of each point show the standard deviation from 12 times of the measurement, (CV=1.4%). As seen from the figure, the absorption line curves. This is due to the discoloring of the indamine dye once formed by the action of superoxide radical, and further shows such assay is not preferable for the assay of guanase.

Experiment 3 (The invented assay)

Figure 3:
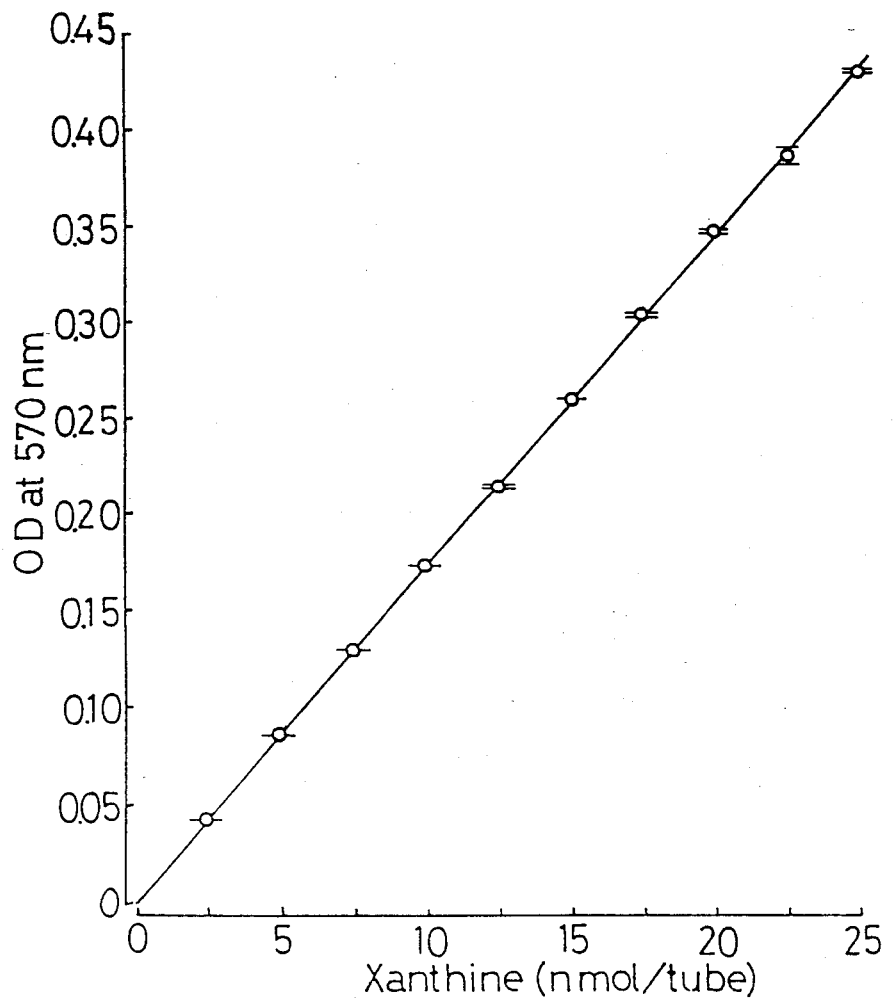
FIG. 3 is a graph showing the state of the coloring when the guanase reaction, the hydrogen peroxide-formation reaction and the coloring reaction are carried out dividedly according to the present invention.

0.4 ml of 0.3 mM guanine buffer solution (pH 8.0) was added to 50 $\mu$l of xanthine solution, and incubated for 13 minutes at 37° C. To this solution, 0.3 ml of 0.2 U X.O was added and further incubated for one minute. To this incubated, 1.0 ml of a buffer solution (pH 3.0) containing 0.5 mM of MBTH, 30 mM of DEA and 50 U of POX, was further added and incubated for one minutes followed by immediate measurement the optical absorption at 570 nm. The result is shown by FIG. 3.

CV=0.7% (12 times). Correlation coefficient ($\nu$)=0.9999 ($\epsilon$=3.33×10$^4$). From the figure, it is clear that this method is practically useful since the calibration line is linear.

Experiment 4 (Relationship between the kinds of the aniline derivatives and coloring degree)

Figure 4:
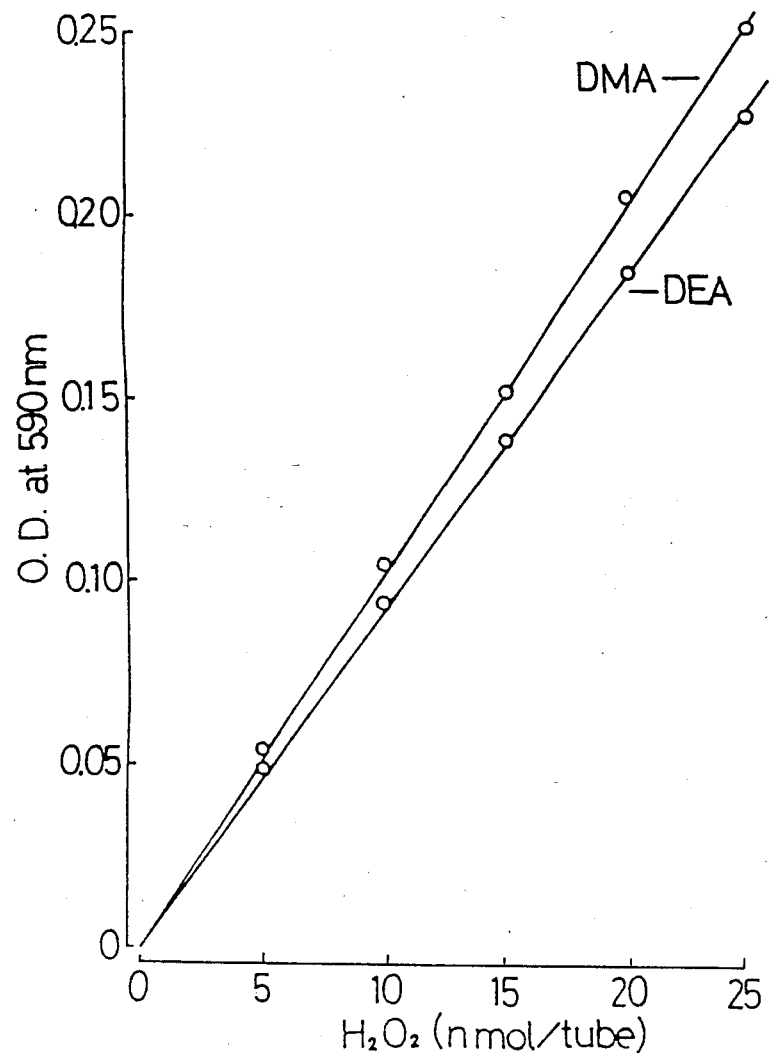
FIG. 4 is a graph showing the change in the coloring depend on the kinds of the aniline derivatives.

To a mixture consisting of 0.1 ml of 0–0.25 mM of hydrogen peroxide and 0.4 ml of 0.3 mM guanine buffer solution (pH 8.0), there were added 1.0 ml of 0.5 mM MBTH, 1.0 mM DMA or DEA and 50 U POX buffer solution (pH 3.0). The mixture was incubated for one minutes at 37° C. followed by the addition of 1.5 ml of 1.5N sulfuric acid and immediate measurement of the optical absorption at 590 nm. As shown by the figure (FIG. 4), the absorption is increased linearly as the amount of hydrogen peroxide added increases and no difference can be seen between the both lines except that the absorption of DMA is slightly strong than that of DEA.

Experiment 5 (Relationship between the guanase activity and the amount of the enzyme)

The relationship between the guanase activity and the amount of the enzyme was surveyed by specimens of partially purified guanase extracted from rat liver. The amount of the crude guanase was measured by Ito et al.'s method aforementioned.

Figure 5:
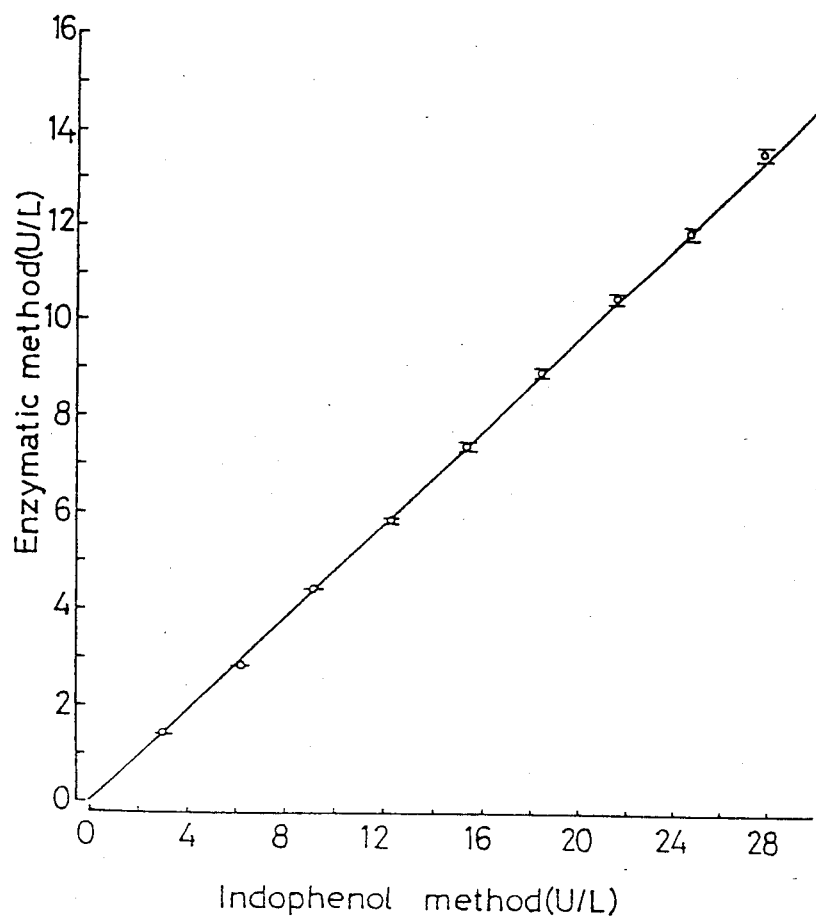
FIG. 5 is a graph showing the correlation between the activity of the guanase and the amount of the enzyme.

On the other hand, the sample which consists of the guanase solution and human serum was assayed according to the Experiment 3. The result is shown by FIG. 5.

As seen from the figure, there is a distinct relationship between the activity of guanase and the amount of the enzyme. In the figure, the short lines holding the upper and lower sides of each point show the standard deviation when the measurement was repeated for 12 times. CV=1.4%, $\nu$=0.9999.

EXAMPLE

Specimens according to the invention.
(1) Buffer solution A
   Each pack for 100 specimens contains 0.215 g of KH$_2$PO$_4$ and 3.998 g of K$_2$HPO$_4$. 5 packs are wrapped in a retort pouch.
(2) Buffer solution B
   Each pack for 100 specimens contains 4.096 g of citric acid, 1.564 g of Na$_2$HPO$_4$, 26.96 mg of MBTH and 1.393 g of DEA. 5 packs are wrapped in a retort pouch.
(3) 3 mM Guanine
   13.62 mg of guanine and 21.94 mg of NaN$_3$ are dissolved in 30 ml of 12 mM NaOH and enclosed in a vial bottle—one bottle
(4) 12 mM NaOH
   21.94 mg of NaN$_3$ is dissolved in 30 ml of 12 mM NaOH solution and enclosed in a vial bottle.—one bottle
(5) 10 U/ml Xanthine oxidase
   Xanthine oxidase is suspended in 26 ml of 3.2M (NH$_4$)$_2$SO$_4$ solution so as to form the above concentration and enclosed in a vial bottle—one bottle
(6) 12,500 U peroxidase
   12,500 U of freeze-dried peroxidase is enclosed in a 10 ml vial bottle—five bottles
(7) 0.5 mM Xanthine
   10 ml for 100 specimens of 0.5 mM xanthine solution are enclosed in a vial bottle—one bottle The above packaged is stable for long period as far as it is stored in a cool place as it is.

[Preparation of operative reagents]

The above packages are available for preparation of the reagents for one day's use.

(1) The substrate buffer solution

The content in one pack of the buffer solution A is dissolved in distilled water to form 200 ml of the solution. 45 ml of this solution are admixed with 5 ml of 3 mM guanine (Reagent I).

(2) The buffer solution without the substrate (for blind test)

To the diluted solution of the buffer solution A in (1), above, 5 ml of 12 mM NaOH are added (Reagent II)

(3) Xanthine oxidase solution

To 5 mL of xanthine oxidase suspension (10 U/ml) 45 ml of the diluted solution of the buffer solution A in (1) are added (Reagent III).

(4) Chromogenic solution

The content in one pack of the buffer solution B is solved in distilled water to form 250 ml of the solution. Then one bottle of the peroxidase is further dissolved in the solution (Reagent IV).

[Procedures for assay]

0.4 ml of Reagent I is added 50 μl of serum specimen and incubated for 13 minutes at 37° C. To this reaction solution, 0.2 ml of Reagent III is added and incubated for one minute followed by the further addtion of 1 ml of Reagent IV. and putting off for one minutes at the same temperature. Thereafter, the optical absorption at 570 nm or difference between 570 nm and 700 nm is immediately measured. The guanase activity can be obtained by predestined calibration line. Besides, if the assay is carried out by automatic analyser, the data corresponding to each point on the calibration line should previously be input into the inner computer of the analyser. The data can be digitally printed out through an A/D converter.

By using such automatic analyser, many items for test (for example, 12 items by Hitachi 706 D analyser) can simultaneously be assayed and the results are immediately printed out without any manual operation excepting set of specimens and reagents, and inital input of the data to computer such as items to be measured, sample numbers, assaying methods, dispensor numbers, test tube numbers normal range, correlation value etc. Thus, the use of such analyser is most preferable for mounting this invented assay on the clinical routine test.

The influence due to other ingredients in blood and purity or factors of the reagents can be avoided by blined test. The Reagent II which not contain guanine is used to determine the blank value for the blined test. The Hitachi's apparatus aforementioned has a control function for the blined test.

As hereinbefore fully described, the present invention can epoch-makingly shorten the required time for the assay of guanase and thereby this assay can be applied for automatic analysis for guanase as a routine work. Therefore, this invention is, in its turn, valuable for diagnosis and treatment of liver diseases, and further it is available for preventing the transfusion hepatitis.

What we claimed is:

1. In the method of assaying guanase in the sample of the body fluid by adding guanine to said sample whereby said guanine is changed to xanthine, decomposing said xanthine to uric acid by xanthine oxidase whereby hydrogen peroxide is by-produced, reacting said hydrogen peroxide with 3-methyl-2-benzothiazolinonehydrazone and an aniline derivative in the presence of peroxidase whereby an indamine dye is produced, and finally measuring the optical absorption by said dye at 570–600 nm, the improvement for rapidly assaying the guanase comprising
   (a) the reactions (I), (II), and (III) being separately and sequentially carried out;
      (I) the xanthine-formation reaction,
      (II) the hydrogen peroxide-formation reaction and
      (III) the dye-producing reaction,
   (b) the xanthine-formation-reaction being carried out within a pH in the range of 7–9, and (c) the hydrogen peroxide-formation reaction being carried out in the presence of a catalase inhibitor.

2. A rapid assaying method for guanase according to claim 1, wherein the aniline derivative is a member selected from the group consisting of N,N-di-loweralkyl anilines.

3. A rapid assaying method for guanase according to claim 1, wherein the catalase inhibitor is sodium azide.

4. A rapid assaying method for guanase according to claim 1, wherein the xanthine formation reaction is carried out within a range of pH 7–9.

5. A rapid assaying method for guanase according to any one of claim 1–4, wherein the assay is carried out by clinically acceptable automatic chemical analyser.

6. A rapid assaying method for guanase according to claim 1, wherein the xanthine formulation reaction is carried out at about pH 8.

* * * * *